United States Patent [19]

Peglion et al.

[11] Patent Number: 5,593,989
[45] Date of Patent: Jan. 14, 1997

[54] TETRACYCLIC 1,4-OXAZINE COMPOUNDS

[75] Inventors: Jean-Louis Peglion, Le Vesinet; Joel Vian, Chaville; Bertrand Goument, Viroflay; Mark Millan, Paris; Valérie Audinot, Croissy sur Seine; Jean-Charles Schwartz, Paris; Pierre Sokoloff, Le Plessis Bouchard, all of France

[73] Assignee: Adir et Compagnie, Courbevoie, France

[21] Appl. No.: 456,504

[22] Filed: Jun. 1, 1995

[30] Foreign Application Priority Data

Jun. 8, 1994 [FR] France ........................ 94 06985

[51] Int. Cl.$^6$ ................. A61K 31/535; C07D 498/04; C07D 498/14
[52] U.S. Cl. .................. 514/229.5; 544/99; 546/62; 546/65
[58] Field of Search ............ 544/99; 514/229.5

[56] References Cited

U.S. PATENT DOCUMENTS 4,420,480  12/1983  Jones ........................... 424/248.4
4,774,243   9/1988  Baldwin ........................ 514/229.5

OTHER PUBLICATIONS

Dewald et al Chemical Abstract 108:94576r (1987).

*Primary Examiner*—Philip I. Datlow
*Attorney, Agent, or Firm*—The Firm of Gordon W. Hueschen

[57] ABSTRACT

New compounds of formula:

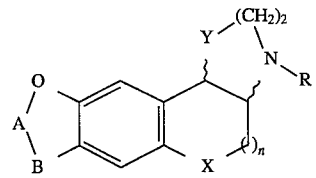

wherein A—B, X, Y, R and n are as defined in the description.

The geometric isomers, racemate and optical isomers thereof and the addition salts with pharmaceutically acceptable acids, and medicinal products containing the same are useful for treating psychotic disorders, depression, Parkinson's disease, memory disorders and disorders associated with drug abuse.

4 Claims, No Drawings

TETRACYCLIC 1,4-OXAZINE COMPOUNDS

The present invention relates to new tetracyclic piperazine and oxazine compounds, a process for their preparation and pharmaceutical compositions containing them.

It relates more especially to compounds of the general formula (I)

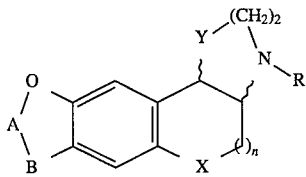

wherein:

X and Y, which may be the same or different, each represents an oxygen atom or $CH_2$;

A—B represents $-(CH_2)_2-$ or $-HC=CH-$ and, in addition:
 when Y represents an oxygen atom, A—B may also represent $-(CH_2)_3-$ and
 when Y represents $CH_2$, A—B may also represent

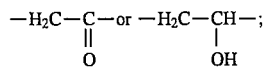

R represents a hydrogen atom or a $(C_1-C_{10})$alkyl, $(C_3-C_{10})$alkenyl or $(C_3-C_{10})$alkynyl radical, each of which may be in straight or branched chain and each of which may optionally be substituted by a cycloalkyl radical having from 3 to 8 carbon atoms, or by an aryl radical selected from the radicals phenyl, thienyl and pyridyl, each of which may optionally be substituted by one or more substituents selected from halogen atoms, hydroxy radical and alkyl and alkoxy radicals each having from 1 to 6 carbon atoms in straight and in branched chain; and n represents:
 0 or 1 when X represents $CH_2$ and
 1 only, when X represents an oxygen atom.

It is possible for the products of the invention to exist in two geometric isomer forms, cis and trans. Those two forms are included in the present invention. Similarly, the presence of asymmetric carbon atoms implies that the molecules of the invention exist in the form of a racemic mixture or racemate and in the form of optical isomers or enantiomers, to which the present invention also extends. In addition, the compounds of the invention may form salts with pharmaceutically acceptable organic or inorganic acids, which salts also form part of the present invention.

The closest prior art to the present invention relates to:
benzopyran compounds having the structure:

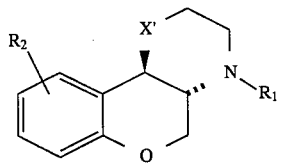

wherein:
X' represents an oxygen atom (EP 0 246 633) or
X' represents $-CH_2-$ (EP 0 161 218), and also compounds having the structure:

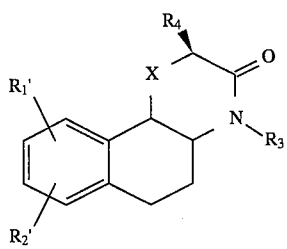

described in the Application WO 93 24471, used in the treatment of disorders of the central nervous system, such as schizophrenia or Parkinson's disease.

Those substances exert their effect on $D_2$ dopaminergic receptors and in that way cause troublesome side effects, such as: an increase in the secretion of prolactin, muscular stiffness or motor retardation and, after prolonged treatment, the development of abnormal involuntary movements (tardive dyskinesia).

Recently, P. Sokoloff et al. (Nature, 1990, 347, 147) demonstrated the existence of a new dopaminergic receptor called $D_3$. Its high concentration in the limb system and its low density in lactotrophic cells and in the nigrostriated system provides a preferred target for obtaining antipsychotic agents that do not have an effect on the secretion of prolactin and that are less likely to cause extrapyramidal-type syndromes.

Studies carried out in vitro (binding to cloned human and rat $D_2$ and $D_3$ receptors) with the compounds of the invention show that they behave like ligands having a high affinity for $D_3$ dopaminergic receptors, whilst exhibiting only low affinity for $D_2$ dopaminergic receptors. The high degree of selectivity of the products of the invention for $D_3$ receptors as opposed to $D_2$ receptors thus makes it possible to envisage, in respect of the products of the invention, a distinct decrease in side effects compared with substances specific to $D_2$.

That selectivity renders the products of the invention valuable most especially for use as medicaments acting on the dopaminergic system, because they would not cause the undesirable effects of $D_2$ ligands.

The compounds of the present invention thus differ from the prior art compounds not only in their chemical structure but also in their pharmacological and therapeutic activity.

The studies carried out in vivo made it possible:

1) to demonstrate in animals the antagonistic activity of the products of the invention to $D_3$ receptors (reversal of hypothermia induced by the $D_3$ prototype agonist: 7-OH—DPAT) according to M. J. Millan's method (Eur. J. Pharmacol., 1994, 260, $R_3$–$R_5$);

2) to demonstrate for the first time the usefulness of such products in the treatment of depression, using the well-known forced-swimming test published in 1978 by Porsolt (Eur. J. Pharmacol, 47, 379–391).

Furthermore, it is generally admitted according to the literature that products acting preferentially on $D_3$ dopaminergic receptors may be used in the treatment of drug abuse (B. Caine, Science, 1993, 260, 1814), as anti-Parkinson's agents (Carlsson, J. Neur. Transm., 1993, 94, 11–19), as antipsychotics and in memory disorders (P. Sokoloff, op. cit.).

The products of the invention thus possess very valuable pharmacological and therapeutic properties and are presented as medicaments for disorders of the central nervous system, in being possible for them to be used as antidepressants, anti-psychotics, anti-Parkinson's agents and anti-mnesics. They are suitable also for the treatment of disorders associated with drug abuse.

The invention extends also to a process for the preparation of the compounds of the invention that belong to the 1,4-oxazine family, that is to say compounds of formula I wherein Y represents an oxygen atom, which process is characterised in that a compound of formula II:

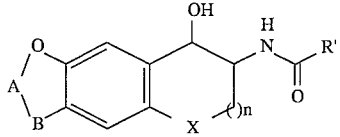
(II)

wherein:

A—B, X and n are as defined hereinbefore, and

R' represents:
- a phenyl, thienyl or pyridyl radical, each of which may optionally be substituted by one or more substituents selected from halogen atoms, hydroxy and alkyl and alkoxy radicals each having from 1 to 6 carbon atoms in straight and branched chain;
- a cycloalkyl radical having from 3 to 8 carbon atoms;
- a $(C_1-C_9)$alkyl, $(C_2-C_9)$alkenyl or $(C_2-C_9)$alkynyl radical each of which may be in straight or branched chain and each of which may optionally be substituted by a cycloalkyl radical having from 3 to 8 carbon atoms, or by an aryl radical selected from the phenyl, thienyl and pyridyl radicals, each of which may optionally be substituted by one or more substituents selected from halogen atoms, hydroxy radical and alkyl and alkoxy radicals each having from 1 to 6 carbon atoms in straight and branched chain, is reduced to obtain a compound of formula III:

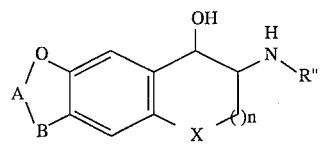
(III)

wherein:

A—B, X and n are as defined hereinbefore, and

R" has the same meaning as R with the exception of hydrogen and methyl; which compound III is treated with an acid halide of formula IV:

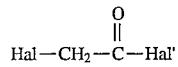
(IV)

wherein Hal and Hal', which may be the same or different, each represents a chlorine or bromine atom, to obtain a compound of formula V:

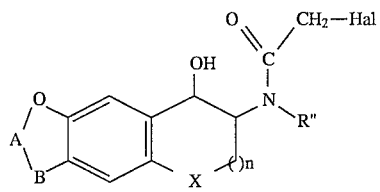
(V)

wherein A—B, X, n, R" and Hal are as defined hereinbefore; which is treated with an alkali metal hydride, such as, for example, sodium hydride, to obtain a compound of formula VI:

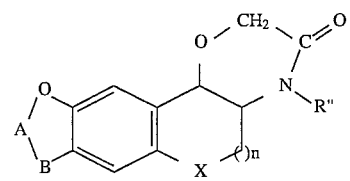
(VI)

wherein A—B, X, n and R" are as defined hereinbefore; which is treated with a lithium aluminium hydride to obtain a compound of formula Ia:

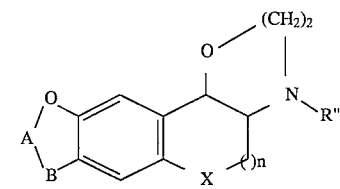
(Ia)

wherein A—B, X, n and R" are as defined hereinbefore, and, if R" represents benzyl, the corresponding compound of formula Ia':

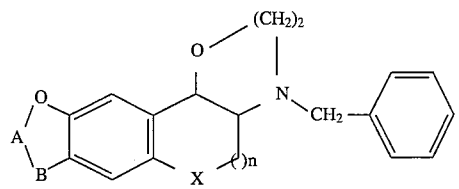
(Ia')

wherein A—B, X and n are as defined hereinbefore, is debenzylated to obtain a compound of formula Ib:

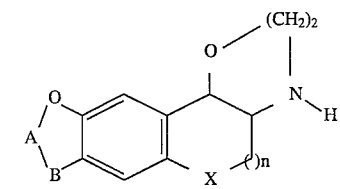
(Ib)

wherein A—B, X and n are as defined hereinbefore; which is in turn treated with a methylating agent to obtain a compound of formula Ic:

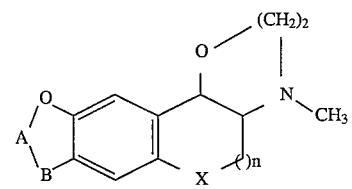
(Ic)

wherein A—B, X and n are as defined hereinbefore.

Alternatively, the compounds of formula I wherein A—B represents —HC=CH—, that is to say compounds corresponding to the formula:

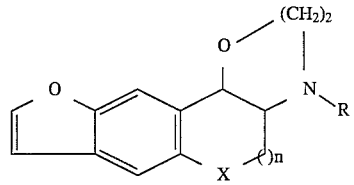

wherein X, n and R are as defined hereinbefore, may also be prepared by oxidation of the corresponding compounds of formula I wherein A—B represents $(CH_2)_2$.

(The oxidation is advantageously effected, for example, by means of 2,3-dichloro-5,6-dicyano-1,4-benzoquinone in acetic acid).

The totality of the compounds of formulae Ia, Ib and Ic form the totality of the compounds of formula I wherein Y represents an oxygen atom.

The reduction of compounds of formula II is advantageously carried out by means of lithium aluminium hydride in a suitable solvent, such as, for example, tetrahydrofuran.

The debenzylation of compounds of formula Ia' is carried out especially satisfactorily by the action of hydrogen, with or without pressure, in the presence of conventional hydrogenation catalysts, such as, for example, Pd/C.

The methylation of compounds of formula Ib is carded out especially suitably by means of a methyl halide, methyl sulphate, methyl phosphate or formaldehyde in formic acid. Concerning the 1,4-oxazine compounds, the starting alcohols of formula II may exist in two geometric isomer forms, cis and trans, of formulae II cis and II trans (II cis)

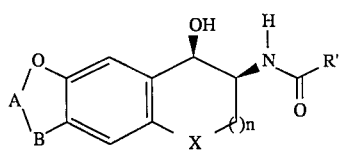

(II trans)

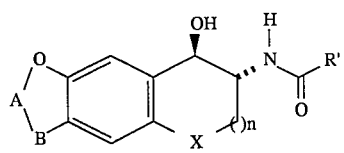

wherein A—B, X, R' and n are as defined hereinbefore. The totality of the compounds of formulae II cis and II trans form the totality of the compounds of formula II.

The II trans compounds are obtained from amino-ketones of formula VII:

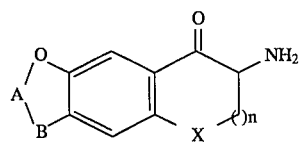            (VII)

wherein A—B, X and n are as defined hereinbefore, which are subjected to a Schotten-Baumann reaction in the presence of an acid halide of formula VIII:

            (VIII)

wherein R' and Hal are as defined hereinbefore, to obtain compounds of formula IX:

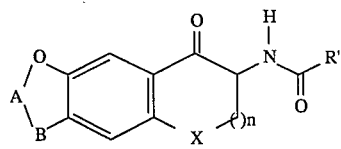            (IX)

wherein A—B, X, n and R' are as defined hereinbefore, which are reduced by an alkali metal borohydride to yield the II trans compounds. The amino-ketones of formula VII are known substances, or may be obtained by known methods from known substances.

The II cis compounds are obtained from azido-ketones of formula X:

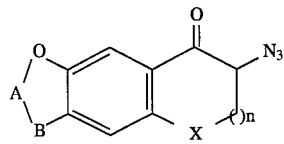            (X)

wherein A—B, X and n are as defined hereinbefore, which, reduced by lithium aluminium hydride, lead to amino alcohols of cis geometry of formula XI:

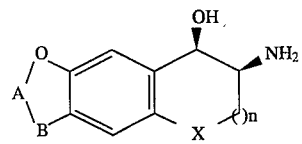            (XI)

wherein A—B, X and n are as defined hereinbefore, which are subjected to the action of an acid halide of formula VIII to yield the II cis compounds.

The azido-ketones of formula X are known substances or are formed by known methods from known substances, as indicated hereinafter in the section relating to the preparation of starting materials.

Similarly, the compounds of formulae III, V, VI, Ia, Ia', Ib and Ic exist in the geometric forms cis and trans.

The invention extends also to a process for the preparation of compounds of the invention that belong to the piperidine family, that is to say compounds of formula I wherein Y represents $CH_2$, which process is characterised in that a compound of formula XII:

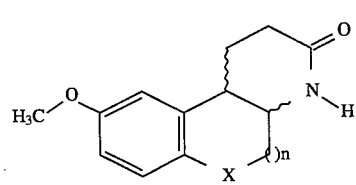            (XII)

wherein X and n are as defined hereinbefore, is reduced to obtain a compound of formula XIII:

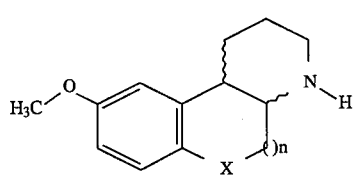            (XIII)

wherein X and n are as defined hereinbefore; which compound is treated with an acid halide of formula VIII:

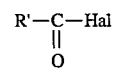            (VIII)

wherein R' and Hal are as defined hereinbefore, to obtain a compound of formula XIV:

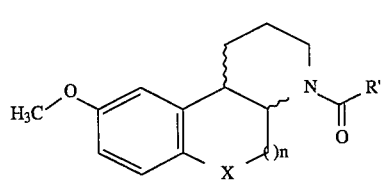            (XIV)

wherein X, n and R' are as defined hereinbefore, which is subjected to the action of boron tribromide in chloroform to obtain a compound of formula XV:

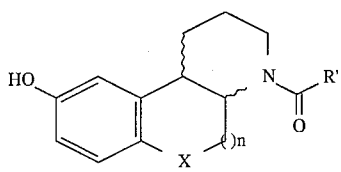

(XV)

wherein X, n and R' are as defined hereinbefore, which is alkylated by way of a Friedel Crafts reaction to obtain a compound of formula XVI:

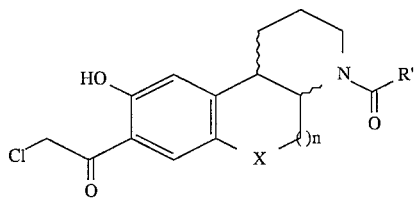

(XVI)

wherein X, n and R' are as defined hereinbefore, which is cyclised in basic medium to obtain a compound of formula XVII:

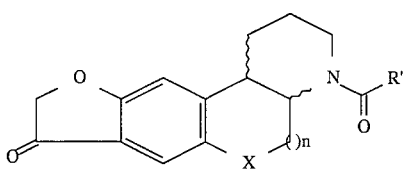

(XVII)

wherein X, n and R' are as defined hereinbefore, which is reduced by sodium borohydride to obtain a compound of formula XVIII:

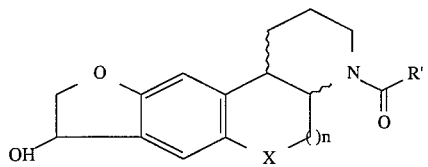

(XVIII)

wherein X, n and R' are as defined hereinbefore, which is dehydrated in acid medium to obtain a compound of formula XIX:

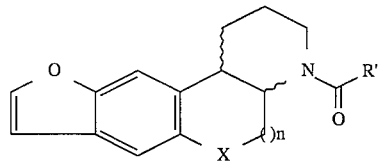

(XIX)

wherein X, n and R' are as defined hereinbefore, which is reduced by a solution of sodium bis(2-methoxyethoxy)aluminium hydride in toluene to obtain a compound of formula Id:

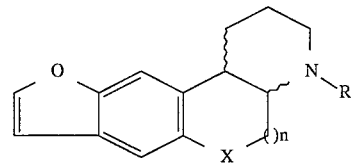

(Id)

wherein X, n and R are as defined hereinbefore, which may optionally be reduced by hydrogen in the presence of a Pt- or Pd-on-carbon catalyst, with or without pressure, to obtain a compound of formula Ie:

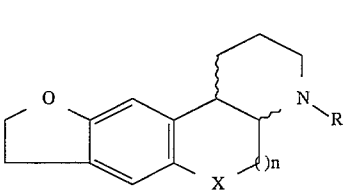

(Ie)

wherein R, X and n are as defined hereinbefore.

The compounds of formula Ie may also optionally be obtained by reducing compounds of formula XVII with borane-dimethyl sulphide.

Reduction of compounds of formula XVII with aluminium hydride, on the other hand, leads to compounds of formula If:

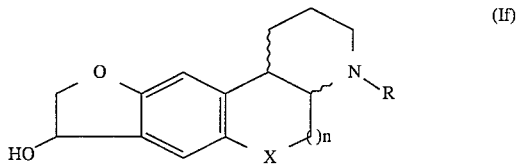

(If)

wherein X, n and R are as defined hereinbefore, which may be oxidised by way of an oxidizing agent, such as manganese dioxide or Jones reagent, to yield compounds of formula Ig:

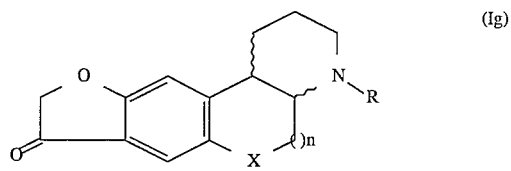

(Ig)

wherein X, n and R are as defined hereinbefore.

Concerning the preparation of compounds that belong to the piperidine family, the compounds of formula XII are reduced either by lithium aluminium hydride in tetrahydrofuran, or by borane-dimethyl sulphide in tetrahydrofuran.

The alkylation of compounds of formula XV is advantageously carried out with chloroacetonitrile in the presence of boron trichloride and aluminium trichloride in methylene chloride.

The cyclisation of compounds of formula XVI is carried out by way of a tertiary amine, such as triethylamine, in chloroform.

The dehydration of compounds of formula XVIII is more advantageously carried out in a mineral acid, such as hydrochloric acid.

Concerning the preparation of compounds that belong to the piperidine family, the starting piperidinones of formula XII may exist in two geometric isomer forms, cis and trans, of formulae XII cis and XII trans:

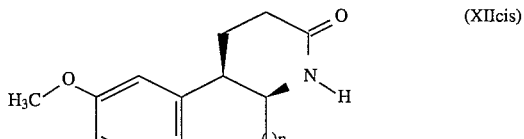

(XIIcis)

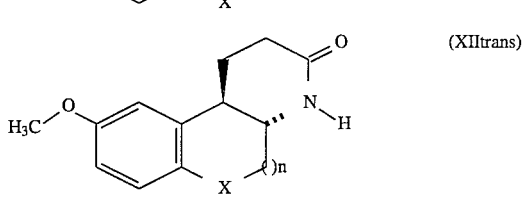

(XIItrans)

wherein X and n are as defined hereinbefore.

The totality of the compounds of formulae XII cis and XII trans form the totality of the compounds of formula XII.

The compounds of formulae XII cis and XII trans are obtained by the reduction of compounds of formula XX:

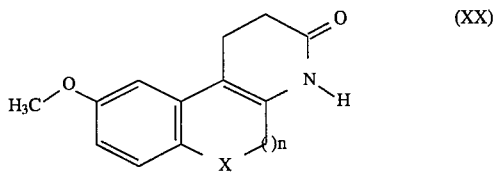

wherein X and n are as defined hereinbefore, the compounds XX themselves being obtained from compounds of formula XXI:

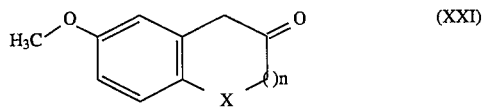

wherein X and n are as defined hereinbefore, by the action of pyrrolidine in the presence of APTS in benzene at reflux, followed by treatment with excess acrylamide at 80° C. then at 140° C.

The compounds of formula XII trans are obtained by the reduction of compounds of formula XX by triethylsilane in methylene chloride in the presence of trifluoroacetic acid, and the XII cis compounds are obtained by catalytic reduction in the presence of Pt/C of compounds of formula XX, after chromatographic separation of the reaction mixture composed of 62% of the XII cis compound and 36% of the XII trans compound.

Similarly, the compounds of formulae XIII, XIV, XV, XVI, XVII, XVIII, XIX, Id, Ie, If and Ig exist in the geometric forms cis and trans.

The following Examples illustrate the invention but do not limit it in any way. The melting points are determined using a Köfler hot plate (K), or a hot plate under a microscope (M.K.). The proton nuclear resonance spectra (NMR) were carried out at 200 MHz (unless indicated to the contrary) using tetramethylsilane (TMS) as internal reference. The chemical shifts are expressed in parts per million (ppm).

EXAMPLE 1 trans-3,4,4a,5,6,8,9,11b-octahydrofuro[2,3-b]1,4-oxazino [3,2-h]4-propyl-2H-naphthalene Step A: N-(8-oxo-2,3,6,7-tetrahydro-5H-naphtho[2,3- b]furan-7-yl)propionamide 23 ml of triethylamine and 5.7 ml of propionyl chloride are added in succession to 17 g of dl-7-amino- 2,3,6,7-tetrahydro-5H-naphtho[2,3-b]furan-8-one hydrochloride suspended in 170 ml of methylene chloride. After 2 hours' stirring at room temperature, the reaction mixture is washed with water, decanted and concentrated to dryness. 20 g of the desired compound are obtained.

M.p.: 162°–164° C. (K) Yield: 100%

Step B: trans-N-(8-hydroxy-2,3,5,6,7,8-hexahydronaphtho [2,3-b]furan-7-yl)propionamide 3 g of sodium borohydride are added in portions to a solution of 20 g of the compound obtained in the preceding Step in 400 ml of ethanol. When the reaction is finished (TLC) the reaction mixture is concentrated in vacuo, taken up in water and extracted with ethyl acetate. The organic phase is dried over magnesium sulphate and concentrated in vacuo to yield 13 g of the desired compound.

M.p.: 182°–184° C. (K) Yield: 65% $^1$H NMR (DMSO d$_6$): 6.9 ppm, s, 1H; 6.8 ppm, s, 1H; 5.2 ppm, 1H exchangeable; 4.45 ppm, t, 2H; 4.3 ppm, t, 1H (J=7.9 Hz); 3.8 ppm, m, 1H (J=7.9 Hz); 3.1 ppm, t, 2H; 2.7 ppm, t, 2H; 2.15 ppm, q, 2H; 1.95 to 1.6 ppm, 2m, 2H; 1 ppm, t 3H.

Step C: trans-N-(8-hydroxy-2,3,5,6,7,8-hexahydronaphtho [2,3-b]furan-7-yl)propylamine 13 g of the compound obtained in the preceding Step, dissolved in 130 ml of tetrahydrofuran, are added dropwise to a suspension of 4.7 g of lithium aluminium hydride in 60 ml of tetrahydrofuran. After 18 hours at room temperature, the reaction mixture is hydrolysed with 3.12 ml of water, followed by 2.5 ml of 20% sodium hydroxide solution then 11.5 ml of water. After filtering off the mineral salts and concentrating the filtrate in vacuo, 11.7 g of the desired compound are obtained.

M.p.: 144°–146 ° C (K) Yield:94%

Step D: trans-N-(8-hydroxy-2,3,5,6,7,8-hexahydronaphtho [2,3-b]furan-7-yl)-N-propyl-2-chloroacetamide 300 ml of a saturated sodium carbonate solution followed by 3.8 ml of chloroacetyl chloride are added to 11.5 g of the compound obtained in the preceding Step dissolved in 600 ml of ethyl acetate. When the reaction is finished (TLC), the reaction mixture is decanted, dried over magnesium sulphate, filtered and concentrated in vacuo. 19 g of the desired compound are obtained.

M.p.: 65°–70° C. (K) Yield: 100%

Step E: trans-4a,5,6,8,9, 11 b-hexahydrofuro[2,3-b]1,4-oxazino[3,2-h]3-oxo-4-propyl-2H-naphthalene A solution of 19 g of the compound obtained in the preceding Step in a mixture of 76 ml of acetonitrile and 380 ml of tetrahydrofuran is added dropwise to a suspension of 6.7 g of sodium hydride (50% in oil) in 50 ml of tetrahydrofuran. When the reaction is finished, excess hydride is decomposed with ethanol, and the reaction mixture is concentrated to dryness, taken up in water and extracted with ethyl acetate. The organic phase is dried over magnesium sulphate and concentrated in vacuo to yield 8.5 g of the desired compound.

M.p. :>260° C (K) Yield: 53%

Step F: Title compound of the Example 8.5 g of the compound obtained in the preceding Step are treated under the same conditions as those used for Step C. 2.5 g of the desired compound are obtained after recrystallisation from ethyl acetate.

M.p.: 92°–94° C. (K) Yield: 34% $^1$H NMR (DMSO d$_6$) 6.9 ppm, s, 1H; 6.7 ppm, s, 1H; 4.5 ppm, t, 2H; 4.1 ppm, d, 1H (J, 8.3 Hz); 3.95 ppm, dd, 1H; 3.75 ppm, td, 1H; 3.15 ppm, t, 2H; 2.8 ppm, m, 4H; 2.3 to 2.15 ppm, m, 3H; 2.05 ppm, m, 1H (J 8.3 Hz); 1.5 ppm, m, 3H; 0.85 ppm, t 3H.

EXAMPLE 2 trans-3,4,4a,5,6,8,9, 11 b-octahydrofuro[2,3-b]1,4-oxazino [3,2-h]4-(2-phenylethyl)-2H-naphthalene Step A: N-(8-oxo-2,3,6,7-tetrahydro-5H-naphtho[2,3- b]furan-7-yl)phenylacetamide This compound is obtained using the method described in Step A of Example 1, but replacing the propionyl chloride with phenylacetic acid chloride.

M.p.: 171°–173° C. (K) Yield: 100%

Step B: trans-N-(8-hydroxy-2,3,5,6,7,8-hexahydro- naphtho [2,3-b]furan-7-yl)benzylamine This compound is obtained by applying the method described in Step B of Example 1 to the compound of the preceding Step.

M.p.: 148°–150° C. (K) Yield: 75% $^1$H NMR (CDCl$_3$) 7.3 ppm, m, 5H; 6.95 to 6.8 ppm, 2s, 2H; 4.5 ppm, t+m, 3H (J, 7.9 Hz); 4.0 ppm, m, 1H; (J, 7.9 Hz); 3.6 ppm, s, 2H; 3.15 ppm, t, 2H; 2.9 ppm, m, 2H; 2.15 to 1.7 ppm, m, 2H.

Step C: trans-N-(8-hydroxy-2,3,5,6,7,8-hexahydro- naphtho [2,3-b]furan-7-yl)2-phenyl ethylamine The desired compound is obtained from the compound of the preceding Step by following the procedure described in Step C of Example 1.

M.p. 144°–148 ° C. (K) Yield: 67%

Step D: trans-N-(8-hydroxy-2,3,5,6,7,8-hexahydro- naphtho [2,3-b ]furan-7-yl)-N-(2-phenyl ethylamine)-2-chloroacetamide This compound is obtained in the form of a foam from the compound of the preceding Step in accordance with Step D of Example 1.

Yield: 100%

Step E: trans-4a,5,6,8,9,11 b-hexahydrofuro[2,3-b]1,4-oxazino[3,2-h]3-oxo-4-(2-phenyl ethyl)-2H- naphthalene This compound is obtained from the compound of the preceding Step in accordance with Step E of Example 1.

M.p.:214°–216° C. (K) Yield:34%

Step F: Title compound of the Example.

By applying to the compound of the preceding Step the method described in Step F of Example 1, the title compound is obtained after recrystallisation from diisopropyl ether.

M.p.: 98°–100° C. (K) Yield: 10% $^1$H NMR (CDCl$_3$) 7.4 to 7.1 ppm, m, 5H; 6.95 to 6.85 ppm, 2s, 2H; 4.5 ppm, t, 2H; 4.25 ppm, d, 1H, (J, 8.5 Hz); 4.15 to 3.8 ppm, 2dd, 2H; 3.2 to 2.5 ppm, m, 10H (J=8.5 Hz); 2.3 ppm, m, 2H; 1.7 to 1.5 ppm, m, 1H.

EXAMPLE 3 trans-3,4,4a,5,6,8,9,11 b-octahydrofuro[2,3-b ]1,4-oxazino [3,2-h]4-(cyclopropylmethyl)-2H-naphthalene This compound is obtained in accordance with the method of Example 1, but with replacement of the propionyl chloride in Step A with cyclopropanecarboxylic acid chloride.

M.p.: 98°–100° C. (K) Yield: 4% (7 Steps) $^1$H NMR (CCDCl$_3$) 6.95 and 6.80 ppm, 2s, 2H; 4.5 ppm, t, 2H; 4.25 ppm, d, 1H, (J=8.5 Hz); 4.0 ppm, 2dd, 2H; 3.1 ppm, m, 3H (J=8.5 Hz); 3.0 to 2.7 ppm, m, 3H; 2.55 ppm, t, 1H; 2.4 to 2.1 ppm, m, 3H; 1.55 ppm, m, 1H; 0.9 ppm, m, 1H; 0.55 ppm, m, 2H; 0.15 ppm, m, 2H.

EXAMPLE 4 cis-3,4,4a,8,9,11 b-hexahydrofuro[2,3-g]1,4-oxazino[5,6-c]4-propyl-5H-benzopyran Step A: cis-2,3,7,8-tetrahydro-3-amino-4-hydroxyfuro[2,3-g]benzopyran Over a period of 1 hour, 2,3,7,8-tetrahydro-3-azido-4-oxofuro[2,3-g]benzopyran (see Preparation 2) dissolved in 300 ml of THF is added to 8.1 g of lithium aluminium hydride suspended in 200 ml of THF at room temperature. After 18 hours at room temperature, the reaction mixture is hydrolysed with 5.6 ml of water, then 4.5 ml of 20% sodium hydroxide solution, then 20.4 ml of water. After filtering off the mineral salts, then concentrating the filtrate using an evaporator, the residue obtained is purified by the acid-base exchange technique to yield 15 g of the desired compound.

Yield: 51%

Step B: cis-2,3,7,8-tetrahydro-3-propionylamino-4-hydroxyfuro[2,3-g]benzopyran 2.5 g of the compound of the preceding Step are treated as described in Step D of Example 1 (using propionyl chloride instead of 2-chloroacetyl chloride) to yield 1.6 g of the desired compound.

M.p.: 192° C. (K) Yield: 51% NMR 400 MHz (DMSO-d$_6$): 7.5 ppm, d, 1H; 6.7 ppm, s, 1H; 6.6 ppm, s, 1H; 5.6 ppm, d, 1H; 4.5 ppm, m, 3H; 4.1 ppm, m, 1H; 3.9 ppm, d, 2H; 3.1 ppm, t, 2H; 2.2 ppm, q 2H; 1.0 ppm, t, 3H.

Demonstration of the cis isomerism by the presence of a Nuclear Overhauser Effect between the proton at 4.5 ppm (proton carried by the carbon carrying the OH) and the proton at 4.1 ppm (proton carried by the carbon carrying the NH).

Step C: cis-2,3,7,8-tetrahydro-3-propylamino-4-hydroxyfuro[2,3-g]benzopyran 1.5 g of the compound of the preceding Step are treated with lithium aluminium hydride as described in Step C of Example 1 to yield, after flash chromatography, 1 g of the desired compound in the form of an oil.

Yield: 70%

Step D: cis-2,3,7,8-tetrahydro-3-(N-propyl-2-chloroacetamido)-4-hydroxyfuro[2,3-g]benzopyran 1 g of the compound of the preceding Step is treated with 2-chloroacetyl chloride as described in Step D of Example 1 to yield 1.05 g of the desired compound in the form of a foam.

Yield: 81%

Step E: cis-4a,8,9,11 b-tetrahydrofuro [2,3-g]1,4- oxazino [5,6-c]3-oxo-4-propyl-2H,5H-benzopyran 1 g of the compound of the preceding Step is treated with sodium hydride as described in Step E of Example 1 to yield 0.86 g of the desired compound in the form of a foam.

Yield:97%

Step F: cis-3,4,4a,8,9,11b-hexahydrofuro [2,3-g]1,4-oxazino[5,6-c]4-propyl-5H-benzopyran 0.81 g of the compound of the preceding Step are treated with lithium aluminium hydride as described in Step F of Example 1 to yield, after flash chromatography, 0.21 g of the desired compound in the form of the free base.

NMR (CDCl$_3$): 6.7 ppm, s, 2H; 4.7 to 4.4 ppm, m, 4H; 4.1 ppm, d, 1H; 3.9 ppm, m, 2H; 3.0–3.3 ppm, m, 3H; 2.8 to 2.5 ppm, m, 4H; 1.55 ppm, m, 2H; 0.95 ppm, t, 3H.

This product is taken up in 10 ml of diethyl ether and 0.4 ml of 2.3N ethereal hydrogen chloride (1.1 eq.) are added thereto, and then the solid formed is filtered through a frit, rinsed with diethyl ether and dried in vacuo to yield 0.22 g of the desired compound in hydrochloride form.

M.p.: 122°–125° C. (MK) Yield: 30% NMR (DMSO-d$_6$+ NaOD): 6.65 ppm, s, 1H; 6.55 ppm, s, 1H; 4.5 to 4.3 ppm, m, 3H; 4.3 ppm, dd, 1H; 4.0 ppm, dd, 1H; 4.0 ppm, dd, 1H; 3.65 ppm, m, 2H; 3.1 ppm, t, 2H; 2.85 ppm, m, 1H; 2.7 to 2.4 ppm, m, 4H; 1.45 ppm, m, 2H; 0.85 ppm, t, 3H.

EXAMPLE 5 trans-3,4,4a,8,9,11b-hexahydrofuro[2,3-g]1,4-oxazino[5,6-c]4-propyl-5H-benzopyran Step A: 2,3,7,8-tetrahydro-3-propionylamino-4-oxofuro[2,3-g]benzopyran 7.25 g of the product obtained in Preparation 3 are treated as described in Step D of Example 1 (using propionyl chloride instead of 2-chloroacetyl chloride) to yield 7.3 g of the desired compound.

M.p.: 184° C. (K) Yield: 94%

Step B: trans-2,3,7,8-tetrahydro-3-propionylamino-4-hydroxyfuro[2,3-g]benzopyran 6.5 g of the product of the preceding Step are treated with sodium borohydride as described in Step B of Example 1 to yield 5.5 g of the desired compound.

Yield: 84% NMR 400 MHz (DMSO-d$_6$): 7.7 ppm, d, 1H; 6.7 ppm, s, 1H; 6.65 ppm, s, 1H; 5.55 ppm, d, 1H; 4.45 ppm, t, 2H; 4.35 ppm, m, 1H; 4.1 ppm, m, 1H; 3.9 ppm, m, 2H; 3.1 ppm, m, 2H; 2.15 ppm, m, 2H; 1.0 ppm, t, 3H.

Demonstration of the trans isomerism by the presence of a Nuclear Overhauser Effect between the protons at 4.35 and 4.1 ppm.

Step C: trans-2,3,7,8-tetrahydro-3-propylamino4- hydroxyfuro[2,3-g]benzopyran 5.4 g of the compound of the preceding Step are treated with lithium aluminium hydride as described in Step C of Example 1 to yield, after recrystallisation twice from ethyl acetate, 2.8 g of the desired compound.

M.p.: 136°–138° C. (K) Yield: 55%

Step D: trans-2,3,7,8-tetrahydro-3-(N-propyl-2-chloroacetamido)-4-hydroxyfuro[2,3-g]benzopyran 2.7 g of the compound of the preceding Step are treated with 2-chloroacetyl chloride as described in Step D of Example 1 to yield 3.5 g of the desired compound in the form of a foam.

Yield: 100%

Step E: trans-4a,8,9, 11 b-tetrahydrofuro[2',Y-g]1,4- oxazino [5,6-c ]3-oxo-4-propyl-2H,5H-benzopyran 3.4 g of the compound of the preceding Step are treated with sodium hydride as described in Step E of Example 1 to yield, after flash chromatography, 2.35 g of the desired compound.

M.p.: 185° C. (K) Yield: 78%

Step F: trans-3,4,4a,8,9,11 b-hexahydrofuro [2,3-g]1,4-oxazino [5,6-c]4-propyl-5H-benzopyran 2.25 g of the compound of the preceding Step are treated with lithium aluminium hydride as described in Step F of Example 1 to yield, after flash chromatography followed by recrystallisation from ethyl acetate, 0.16 g of the desired compound in the form of the free base.

M.p.: 117°–119° C. (K) Yield: 7% NMR (CDCl$_3$): 6.8 ppm, s, 1H; 6.6 ppm, s, 1H; 4.5 ppm, m, 3H; 4.4 ppm, d, 1H (J=9.2 Hz); 4.05 ppm, dd, 1H; 3.9 ppm, dd, 1H; 3.85 ppm, m, 1H; 3.15 ppm, t, 2H; 2.9 ppm, dd, 1H; 2.7 ppm, m, 1H; 2.4 to 2.6 ppm, m, 2H; 2.25 ppm, m, 1H; 1.7 to 1.4 ppm, m, 2H; 0.95 ppm, t, 3H.

EXAMPLE 6 trans-3,4,4a,11b-tetrahydrofuro[2,3-g]1,4-oxazino[5,6-c]4-propyl-5H-benzopyran 0.72 g (2.6 mmol) of the title compound of Example 5 is dissolved in 100 ml of acetic acid. 20 ml of water are added in one go, followed by 2.8 g (7.8 mmol), in portions, of 2,3-dichloro-5,6-dicyano-1,4-benzoquinone. The whole is heated at reflux for 12 hours, then 0.9 g (3.9 mmol) of 2,3-dichloro-5,6-dicyano-1,4-benzoquinone are added in portions and the whole is heated at reflux again for 10 hours. The mixture is allowed to cool, evaporated to dryness and purified by flash chromatography on silica (eluant: CH$_2$Cl$_2$/CH$_3$COOEt: 90/10). 0.17 g of the expected product, of which the hydrochloride melts at 200°–205° C., is obtained.

EXAMPLE 7 trans-4-aza-1,2,3,4,4a,5,6,11b-octahydro-4-propylfuro[2,3-b]phenanthrene

Step A 9-methoxy-1,4,5,6-tetrahydrobenzo[f]quinolin-3-(2H)-one 15.6 g of pyrrolidine in 145 ml of benzene are added dropwise to a solution of 25 g of 7-methoxy-2-tetralone in 285 ml of benzene and a catalytic amount of paratoluenesulphonic acid heated at reflux. After the theoretical amount of water has been obtained, the benzene is evaporated off under reduced pressure and 62.4 g of acrylamide are added. The reaction mixture is heated for 90 minutes at 80° C. and then for 30 minutes at 140° C. After cooling, the mixture is taken up in methylene chloride, then washed with water, dried over magnesium sulphate and subsequently evaporated to dryness. The residue is recrystallised from acetic acid to yield 10.3 g of the expected product.

M.p. 232°–234° C. (K) Yield: 32%

Step B: trans-9-methoxy- 1,4,4a,5,6,10b-hexahydrobenzo[f]quinolin-3-(2H)-one 10.4 g of triethylsilane are added to a solution of 7 g of the compound obtained in the preceding Step in 80 ml of dichloromethane. The mixture is stirred for 10 minutes at room temperature. 39 ml of trifluoroacetic acid are then added while cooling the mixture with an ice bath. The mixture is stirred for 18 hours at room temperature. After evaporation of the solvent using a rotary evaporator, a yellow oil is obtained which is dissolved in dichloromethane. The organic phase is washed with a sodium hydrogen carbonate solution until a basic pH is obtained, and dried over magnesium sulphate, and the solvent is evaporated off using a rotary evaporator. The residue is taken up in hexane, and the whole is decanted and solidified in acetonitrile. 6.3 g of the expected isomer are obtained.

M.p.:222°–224° C. (K) Yield: 74% NMR 400 MHz: (CDCl$_3$) $^1$H spectrum: 7.1 ppm (d, 1H); 6.85 ppm (dd, 1H); 6.75 ppm (dd, 1H); 3.8 ppm (s, 3H); 3.4 ppm (m, 1H, J=11Hz); 2.9 ppm (m, 2H); 2.7 ppm (m, 1H, J=1 1Hz); 2.65 ppm (m, 3H); 2.1/1.9 ppm (m, 2H); 1.75 ppm (m, 1H); 7.7 ppm (s, 1H). J=1 1Hz: trans ring junction isomerism.

Step C: trans-9-methoxy- 1,2,3,4,4a,5,6,10b-octahydrobenzo[f]quinoline

A solution of 8.3 g of the compound obtained in Step B in 83 ml of tetrahydrofuran is added dropwise to a suspension of 6.2 g of lithium aluminium hydride. After 18 hours' reflux, the mixture is hydrolysed in succession by 4.1 ml of water, 3.3 ml of 20% sodium hydroxide solution and 15.4 ml of water. After filtering off the mineral salts, then concentrating the filtrate using a rotary evaporator, 4.5 g of the expected product are obtained.

M.p.: 68°–70° C. (K) Yield: 60%

Step D: trans-9-methoxy-4-propionyl- 1,2,3,4,4a,5,6,10b-octahydrobenzo[f]quinoline 3.7 ml of triethylamine, followed by 1.8 ml of propionyl chloride are added at room temperature to a solution of 4.5 g of the compound obtained in the preceding Step in 45 ml of dichloromethane. The mixture is stirred for 18 hours at room temperature. After evaporation of the solvent using a rotary evaporator, the residue is taken up in ethyl acetate, washed with water and dried over magnesium sulphate and the solvent is concentrated to dryness. Purification by flash chromatography yields 5 g of the expected product.

Yield: 86%

Step E: trans-9-hydroxy -4-propionyl- 1,2,3,4,4a,5,6, 10b-octahydrobenzo[f]quinoline A solution of 6.8 g of the compound obtained in Step D in 72 ml of chloroform is cooled to 0° C., then 5.3 ml of boron tribromide are added dropwise thereto. The whole is stirred for 18 hours at room temperature before the addition of 20 ml of ethanol. The resulting precipitate is filtered and washed with water, and 5.1 g of the expected compound are thereby isolated.

Yield: 79%

Step F: trans-8-[(2-chloro-1-oxo)ethyl]9-hydroxy-4- propionyl- 1,2,3,4,4a,5,6, 10b-octa hydro-benzo[f]quinoline 47 ml of a 1M boron trichloride solution in dichloromethane are cooled to 0° C. There are added in portions thereto 5.1 g of the compound described in the preceding Step followed by 3 ml of chloroacetonitrile and then 2.6 g of anhydrous aluminium chloride. The whole is left for 4 hours at 0° C. with stirring and then for 18 hours at room temperature before hydrolysis in succession with 12.2 ml of water and 22 ml of 10% hydrochloric acid with cooling. Concentrated ammonia is added until a basic pH is reached. The whole is decanted, the aqueous phase is extracted with dichloromethane, and the organic phase is washed with water and dried over anhydrous magnesium sulphate. After evaporation of the solvent in vacuo, 5.9 g of expected product are obtained.

M.p.: 177°–179° C. (K) Yield: 89%

Step G: trans-4-aza-1,2,3,4,4a,5,6,11 b-octahydro(9H)4-propionylfuro[2,3-b]phenanthren-8-one 8.3 g of the compound obtained in the preceding Step in 142 ml of dichloromethane and 17.8 ml of triethylamine are stirred at reflux for 2 hours 30 minutes. After evaporation of the solvent in vacuo, the residue is treated with water and extracted with ethyl acetate. The organic phase is decanted off and dried over anhydrous magnesium sulphate, yielding 5 g of the expected product.

M.p.: 172°–176° C. (K) Yield :95%

Step H: trans-1-(8-hydroxy-1,2,3,4,4a,5,6,8,9,11b- decahydro4-azafuro[2,3-b]phenan thren-4-yl)propan-1-one 20 ml of a 10% solution of sodium hydrogen carbonate and 1.23 g of sodium borohydride are added in portions, at room temperature, to a solution of 4.9 g of the compound obtained in the preceding Step in 41 ml of methanol. After evaporation of the solvent using a rotary evaporator, the residue is taken up in ethyl acetate, washed with water and dried over magnesium sulphate and the solvent is concentrated in vacuo. 3 g of the expected product are obtained.

Yield: 61%

Step I: trans-1-(1,2,3,4,4a,5,6,11b-octahydro-4-azafuro[2,3-b]phenanthren-4-yl)propan-1-one 3 g of the compound obtained in the preceding Step in 18.7 ml of 10% hydrochloric acid are maintained under magnetic stirring for 4 hours. The whole is extracted with dichloromethane, decanted, washed with N sodium hydroxide solution and dried over anhydrous magnesium sulphate. After evaporation of the organic phase in vacuo, 2.3 g of the expected product are isolated.

Yield: 81.5%

Step J: title compound of Example 7 (in its hydrochloride form)

To a solution of 0.55 g (1.94 mmole) of the compound obtained in the preceding step, in 13.7 ml of toluene, is added 1.66 ml (5.82 mmole) of a 3.5 M solution of Red-Al® in toluene. Then the mixture is stirred for 3 hours at room temperature. After hydrolysis by 0.75 ml of ethanol and 1 ml of water, the mineral salts are filtered off and the organic phase is extracted by HCl 1N. The acidic phase is basified by NaOH 1N and extracted twice with methylene chloride and the organic phase is dried over magnesium sulphate. After evaporation of the solvent in vacuo, the oily residue is taken up in 15 ml of acetonitrile and 0.8 ml of 2.5N etheral hydrogen chloride is added thereto. 0.35 g of the title compound, in the hydrochloride form is filtered off.

M.p.: 235°–238 ° C. (MK) Yield: 59% NMR (DMSO-$d_6$) $^1$H spectrum 11ppm, exchangeable $D_2O$; 7.95 ppm, d, 1H; 7.5 ppm, s,1 H; 7.4 ppm, s, 1H; 6.85 ppm, d, 1H; 3.5 ppm, d, 1H; 3.4 á 2.9 ppm, m, 7H; 2.6 ppm, m, 1H; 2.4 ppm, m, 1H; 2.2 à 1.9 ppm, m, 3H; 1.7 ppm, m, 2H; 1.5 ppm, m, 1H; 1 ppm, t, 3H.

EXAMPLE 8 cis-4-aza-1,2,3,4,4a,5,6,11b-octahydro-4-propylfuro[2,3-b]phenanthrene

The title compound is obtained in the same manner as the compound of Example 7, but using in Step C cis-9methoxy-1,4,4a,5,6,10b-hexahydrobenzo[f]quinolin-3-(2H)-one, which is obtained in the following manner: 0.5 g of the compound obtained in Step A of Example 7 is stirred in 18 ml of acetic acid with 0.2 g of 5% palladium/C for 18 hours at room temperature under 200 g of hydrogen pressure. After removal of the catalyst by filtration and evaporation of the solvent, 0.5 g of residue is chromatographed on a silica column (eluant: $CH_2Cl_2/CH_3COOEt$; 85/15). 0.32 g of the cis compound is thereby obtained.

Yield:62% NMR 400 MHz: ($CDCl_3$) $^1$H spectrum: 7.0 ppm (d, 1H); 6.75 ppm (m, 2H); 6.0 ppm (s, 1H); 3.85 ppm (m, 1H, J=5.5 Hz); 3.8 ppm (s, 3H); 3.2/2.8 ppm (m, 6H); 3.15 ppm (m, 1H, J=5.5 Hz); 2.1 ppm (m, 2H). J=5.5 Hz: cis ring junction isomerism.

PREPARATION OF THE NEW STARTING MATERIALS

Preparation 1: 2,3,7,8-tetrahydro-4-oxofuro[2,3-g]benzopyran

Step A: 3-(2,3-dihydrobenzofuran-5-yloxy)propionitrile 40.8 g of 2,3-dihydro-5-hydroxybenzofuran (the synthesis of which is described in Synthesis 1988, 950–952), 3 ml of a 40% solution of Triton B in methanol and 200 ml of freshly distilled acrylonitrile are mixed at room temperature. The mixture is heated at reflux for 46 hours, then the acrylonitrile is evaporated off as far as possible. The residue is taken up in ethyl acetate, washed with 2N sodium hydroxide solution, N hydrochloric acid and water. The organic phase, dried over magnesium sulphate, is concentrated in vacuo, and then the residue is recrystallised from 300 ml of isopropanol to yield 38 g of the desired compound.

M.p. <50° C. (K) Yield: 67%

Step B: 3-(2,3-dihydrobenzofuran-5-yloxy)propionic acid 10.6 g of the compound of the preceding Step and 21 ml of concentrated hydrochloric acid are heated at reflux for 5 hours. After having cooled, the mixture is extracted with dichloromethane. The combined organic phases are washed with water, and then extracted with a saturated aqueous sodium hydrogen carbonate solution. The basic aqueous phases are acidified in the cold with concentrated hydrochloric acid, and the solid formed is filtered, rinsed with water and dried in vacuo to yield 9.65 g of the desired compound.

M.p.: 131°–132° C. (K) Yield: 82%

Step C: 2,3,7,8-tetrahydro-4-oxofuro[2,3-g]benzopyran 34.1 g of the compound of the preceding Step are added to 46.5 g of phosphoric anhydride in 465 ml of methanesulphonic acid at 60° C. and the whole is stirred for 10 minutes at 60° C. and then poured into 2 l of a water/ice mixture and extracted with diethyl ether. The combined organic phases are washed with N sodium hydroxide solution and with water, then dried over magnesium sulphate and concentrated. The residue is recrystallised from 80 ml of ethanol to yield 20.9 g of the desired compound.

M.p.: 101° C. (K) Yield: 67%

Preparation 2: 2,3,7,8-tetrahydro-3-azido-4-oxofuro[2,3-g]benzopyran

Step A: 2,3,7,8-tetrahydro-3-bromo-4-oxofuro[2,3-g]benzopyran 69.3 g of tetra-n-butylammonium tribromide are added in portions to 27 g of the title compound of Preparation 1 in 1400 ml of dichloromethane and 560 ml of methanol at room temperature. After 5 hours' stirring at room-temperature, the solvents are evaporated off and the residue is taken up in dichloromethane and washed with 2N hydrochloric acid and with water. Drying over magnesium sulphate and evaporation of the solvent yield 38 g, of the desired compound which is used as it is.

Yield: 100%

Step B: 2,3,7,8-tetrahydro-3-azido-4-oxofuro[2,3- g]benzopyran 12 g of sodium azide are added in portions to the product of the preceding Step in 185 ml of DMF at room temperature. After 3 hours' stirring at room temperature, the whole is poured into 2 l of water and extracted with dichloromethane. The combined organic phases are washed with water, dried over magnesium sulphate and then concentrated to yield 31 g of the desired compound, which is used without being purified because of its instability.

Preparation 3: 2,3,7,8-tetrahydro-3-amino-4-oxofuro[2,3-g]benzopyran

Step A: 7,8-dihydro-4-hydroxyiminofuro[2,3-g]benzopyran 27.4 g of 2,3,7,8-tetrahydro-4-oxofuro[2,3-g]benzopyran (see Preparation 1), 42 g of hydroxylamine hydrochloride and 41.9 g of sodium acetate in 288 ml of ethanol are heated at reflux for 1 hour. The solvent is evaporated off and the residue is taken up in dichloromethane and washed with water. After drying over magnesium sulphate, evaporation and then recrystallisation from ethanol, 21.85 g of the desired compound are obtained.

M.p.: 160° C. (K) Yield: 74%

Step B: 2,3,7,8-tetrahydro-4-p-toluenesulphonyloxyiminofuro[2,3-g]benzopyran 24.3 g of tosyl chloride are added in portions to 21.8 g of the product of the preceding Step in 106 ml of pyridine at 0° C. The whole is subsequently stirred for 2 hours at 0° C, then for 24 hours at room temperature, subsequently poured into 1 l of water and extracted with diethyl ether. The combined ethereal phases are washed with water, 0.5N sulphuric acid and water, then dried over magnesium sulphate and concentrated in vacuo to yield 36 g of the desired compound.

M.p.: 118° C. (K) Yield:94%

Step C: 2,3,7,8-tetrahydro-3-amino-4-oxofuro[2,3- g]benzopyran 35.9 g of the product of the preceding Step in 130 ml of benzene are added to sodium ethoxide in ethanol (prepared from 2.64 g of sodium and 100 ml of anhydrous ethanol) at 0° C. After 6 hours' stirring at room temperature, then resting in a refrigerator overnight, the solid formed is filtered and rinsed with benzene. The filtrates are poured into 250 ml of 4N hydrochloric acid with vigorous stirring. The solid formed is filtered and dried in vacuo to yield 18.7 g of the desired compound in hydrochloride form.

M.p. >260° C. (K) Yield: 78%

EXAMPLE 9

Pharmacological Study

The selectivity for $D_3$ receptors as opposed to $D_2$ receptors was demonstrated:

in vitro: by the technique of binding to human and rat $D_2$ and $D_3$ receptors (expressed independently and in a stable manner in CHO cells);

in vivo: by the capacity of the molecules to modulate hypothermia induced in rats by the $D_3$ dopaminergic agonist, 7-OH-DPAT, control of the body temperature being dependent upon the post-synaptic $D_3$ receptor (M. J. Millan, op. cit.).

The therapeutic properties, and especially the anti-depressant properties, were demonstrated using the Porsolt test (forced-swimming test).

A-$D_3$ vs $D_2$ selectivity

1. Materials and method
  1.1 In vitro binding

The affinity of the compounds for human or rat $D_3$ and $D_2$ receptors (expressed independently and in a stable manner in CHO cells) was determined in membrane preparations using [$^{125}$I]-iodosulpiride as radioligand (Sokoloff et al, op. cit.), raclopride (10 μM) determining the non-specific binding. The results are expressed as $IC_{50}$. The selectivity is expressed by the ratio of $IC_{50}$ $D_2$ to $IC_{50}$ $D_3$.

1.2 In vivo hypothermia in rats

The tests were carried out on male Wistar rats weighing 200–250 g, placed in individual cages with free access to food and water. The products were dissolved in distilled water to which several drops of lactic acid are added. The injections were effected in a volume of 1.0 ml/kg by the subcutaneous route. The doses are expressed in base. The rectal temperature of the rats was recorded using a digital thermal probe (Millan et al., J.P.E.T., 1993, 264, p. 1364–1376). The rats were injected with the compound or vehicle, then put back in their cages for 30 minutes. The rats were then given an injection of 7-OH-DPAT (0.16 mg/kg) and put back in their cages. Thirty minutes later, the rectal temperature was measured and the difference to basal values ($\Delta T°$ C.) was determined. The inhibitory dose (95% confidence limit) for reducing the effect of 7-OH-DPAT by 50% was calculated according to Finney's method (Statistical Method in Biological Assays, 2nd ed., Hafner Publishing, New York, 1964).

2. Results 2.1. Binding

The affinities ($IC_{50}$) of the products of the invention for $D_3$ receptors are from $10^{-9}$M to $10^{-7}$M, whilst those for $D_2$ receptors are from $10^{-7}$M to $10^{-5}$M. By way of example, the selectivity for $D_3$ receptors compared with $D_2$ receptors, expressed by the ratio of $IC_{50}$ $D_2$ to $IC_{50}$ $D_3$, is 44 for the cloned rat receptors and 45 for the cloned human receptors in the case of the product of Example 1. Those values compare favourably with those obtained with the specific agonist 7-OH-DPAT for which the $D_3$ vs $D_2$ selectivity is 53 for the cloned rat receptors, and especially with those obtained for the antagonists AJ 76 and (+)UH 232, the selectivity of which is only 2.2 and 4.8 respectively for the cloned human receptors.

2.2 Hypothermia in rats

The effect of the products of the invention on $D_3$ receptors in vivo is illustrated by the behaviour of the compound of Example 1 in a hypothermia model. The values obtained during that test are listed in Table 1.

TABLE 1

| INJECTION 1 | | INJECTION 2 | | $\Delta T °C.$[a] |
|---|---|---|---|---|
| Vehicle | — | — | | +0.6 ± 0.1 |
| Vehicle | — | 7-OH—DPAT | (0.16 mg/kg) | −1.4 ± 0.1 |
| Ex 1 | (0.16 mg/kg) | 7-OH—DPAT | (0.16 mg/kg) | −1.8 ± 0.2 |
| Ex 1 | (0.63 mg/kg) | 7-OH—DPAT | (0.16 mg/kg) | −1.3 ± 0.2 |
| Ex 1 | (2.5 mg/kg) | 7-OH—DPAT | (0.16 mg/kg) | +0.2 ± 0.2* |
| Ex 1 | (10.0 mg/kg) | 7-OH—DPAT | (0.16 mg/kg) | −0.1 ± 0.2* |

[a] the values are means ± sem N > 5–9 per value
*p < 0.05 versus vehicle/7-OH—DPAT according to the Dunnett test.

The inhibitory dose ($ID_{50}$) (95% C.L.=95% confidence limit) is 1.6 (0.7–3.7) mg/kg s.c.. This clearly demonstrates that the products of the invention not only recognize the $D_3$ receptors in vitro but act, in vivo, by way of those same $D_3$ receptors.

B—Therapeutic model

1. Materials and method
Forced-swimming test.

The procedure has been described in detail by Porsolt et al. (1978).

The experiment was carried out over two days, the test taking place on the second day. On the first day, the animal was placed for 15 minutes in a glass cylinder (30 cm×⌀20 cm) filled with water, the temperature of which is maintained at 25° C. On the second day, the day of the test, the product or the solvent was administered to the animal by the subcutaneous route 30 minutes before the beginning of the test, At $T_0$, the animal was placed in a cylinder filled with water for the 5 minutes the test lasted. The total period (expressed in seconds) of immobility of the animal was measured.

The inhibitory dose (95% confidence limit) for reducing immobility time by 50% was calculated according to Finney's method (Statistical Method in Biological Assays, 2nd ed., Hafner Publishing, New York, 1964).

2—Results

In order to illustrate the anti-depressant effect claimed for the products of the invention, the results obtained with one of the compounds representing the invention are reported below (cf. Table 2). In this test, the compound of Example 1 exhibits an inhibitory dose ($ID_{50}$) (95% C.L.=95% confidence limit) of 1.8 (1.2–2.7) mg/kg s.c., thus revealing a powerful anti-depressant effect.

TABLE 2

| Product | Dose (mg/kg) | Period of immobility (sec) |
|---|---|---|
| Vehicle |  | 188.0 ± 15.6 |
| Ex 1 | 0.63 | 200.8 ± 17.4 |
| Ex 1 | 1.25 | 107.1 ± 39.7 |
| Ex 1 | 2.5 | 63.1 ± 12.4* |
| Ex 1 | 10.0 | 28.2 ± 18.1* |

*p < 0.05 versus vehicle/7-OH—DPAT according to the Dunnett test. The values are means ± sem N ≧ 4–7 per value.

We claim:

1. A compound selected from those of formula I

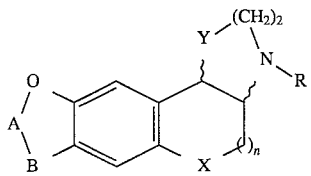

wherein:

X and Y, which may be the same or different, each represents an oxygen atom or $CH_2$;

A—B represents —$(CH_2)_2$— or —HC=CH— and, in addition:
  when Y represents an oxygen atom, A-B may also represent —$(CH_2)_3$— and
  when Y represents $CH_2$, A-B may also represent

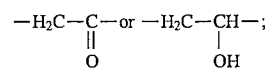

R represents a hydrogen atom or a ($C_1$—$C_{10}$)alkyl, ($C_3$–$C_{10}$)alkenyl or ($C_3$–$C_{10}$)alkynyl radical, each of which may be in straight or branched chain and each of which may optionally be substituted by a cycloalkyl radical having from 3 to 8 carbon atoms, or by an aryl radical selected from the radicals phenyl, thienyl and pyridyl, each of which may optionally be substituted by one or more substituents selected from halogen atoms, hydroxy radicals, and alkyl and alkoxy radicals each having 1 to 6 carbon atoms in straight or in branched chain; and n represents:
  0 or 1 when X represents $CH_2$ and
  1 only, when X represents an oxygen atom their geometric isomer forms, cis and trans,—their racemic mixture or racemate, and their optical isomer or enantiomer forms, and their salts with a pharmaceutically acceptable acid.

2. A compound according to claim 1 which is: 3,4,4a,5,6,8,9,11b-octahydrofuro[2,3-b]1,4-oxazino[3,2-h]4-propyl-2H-naphthalene.

3. A method for treating a mammal afflicted with a condition selected from psychotic disorders, depression, Parkinson's disease, memory disorders, and disorders associated with drug abuse, comprising the step of administering to the mammal an amount of a compound of claim 1 which is effective for alleviation of said condition.

4. A pharmaceutical composition, useful in alleviation of depression comprising as active ingredient an effective amount of a compound of claim 1, together with one or more pharmaceutically acceptable excipients or vehicles.

* * * * *

UNITED STATES PATENT AND TRADEMARK OFFICE
CERTIFICATE OF CORRECTION

PATENT NO. : 5,593,989
DATED : January 14, 1997
INVENTOR(S) : J-L Peglion; J. Vian; B. Goument; M. Millan; V. Audinot; J-C. Schwartz; P. Sokoloff It is certified that error appears in the above-indentified patent and that said Letters Patent is hereby corrected as shown below:

Column 2, line 5: In formula, "$R_1'$" and "$R_2'$" should read -- $R'_1$ -- and -- $R'_2$ --.

Column 12, line 42: Delete second occurrence "1H; 4.0 ppm, dd,".

Column 13, line 1: "-3-propylamino4-" should read -- -3-propylamino-4- --.

Column 13, line 15: "[2',Y-g]" should read -- [2',3'-g] --.

Column 15, line 19: At the beginning of the line, "dro4-" should read -- dro-4- --.

Column 20, line 1: Delete "and Y, which may be the same or different, each".

Column 20, line 2: At end of line after "or $CH_2$;" insert -- and Y represents an oxygen atom; --.

Column 20, line 7: Delete "and" at end of line and insert -- ; --.

Column 20, lines 9-12: Delete the two (2) lines beginning "when" and including the formulas in the next line.

UNITED STATES PATENT AND TRADEMARK OFFICE
CERTIFICATE OF CORRECTION

PATENT NO. : 5,593,989
DATED : January 14, 1997          Page 2 of 2
INVENTOR(S) : J-L Peglion; J. Vian; B. Goument;
M. Millan; V. Audinot; J-C. Schwartz;
P. Sokoloff It is certified that error appears in the above-indentified patent and that said Letters Patent is hereby corrected as shown below:

Column 20, line 15: Insert -- , -- after "alkenyl".

Column 20, line 18: Delete the word "from" before "3".

Column 20, line 33: Insert a -- - -- (hyphen) between "pharmaceutically" and "acceptable".

Column 20, line 48: Insert a -- - -- (hyphen) between "pharmaceutically" and "acceptable".

Signed and Sealed this

Eighth Day of April, 1997

Attest:

BRUCE LEHMAN

Attesting Officer      Commissioner of Patents and Trademarks